United States Patent
Wilson et al.

(10) Patent No.: US 8,112,141 B2
(45) Date of Patent: Feb. 7, 2012

(54) METHOD AND DEVICE FOR QUICK PRESS ON EEG ELECTRODE

(75) Inventors: Scott B. Wilson, Del Mar, CA (US); Mark Scheuer, Wexford, PA (US); Dale Johnson, San Diego, CA (US); Scott Clear, Escondido, CA (US)

(73) Assignee: Persyst Development Corporation, Del Mar, CA (US)

( * ) Notice: Subject to any disclaimer, the term of this patent is extended or adjusted under 35 U.S.C. 154(b) by 930 days.

(21) Appl. No.: 12/125,802

(22) Filed: May 22, 2008

(65) Prior Publication Data

US 2008/0294031 A1 Nov. 27, 2008

Related U.S. Application Data

(60) Provisional application No. 60/939,523, filed on May 22, 2007.

(51) Int. Cl.
*A61B 5/04* (2006.01)

(52) U.S. Cl. ........ 600/383; 600/382; 600/386; 600/393; 600/544

(58) Field of Classification Search .................. 600/372, 600/382–390, 393–396, 509, 544, 547
See application file for complete search history.

(56) References Cited

U.S. PATENT DOCUMENTS

| 4,709,702 | A | | 12/1987 | Sherwin | |
|---|---|---|---|---|---|
| 4,967,038 | A | * | 10/1990 | Gevins et al. | 600/383 |
| 5,038,782 | A | * | 8/1991 | Gevins et al. | 600/383 |
| 5,305,746 | A | * | 4/1994 | Fendrock | 600/391 |
| 6,334,856 | B1 | * | 1/2002 | Allen et al. | 604/191 |
| 7,941,201 | B2 | * | 5/2011 | Chiou et al. | 600/373 |
| 2004/0152957 | A1 | * | 8/2004 | Stivoric et al. | 600/300 |

FOREIGN PATENT DOCUMENTS

| EP | 0137500 | 4/1985 |
|---|---|---|
| EP | 0571120 | 11/1993 |

OTHER PUBLICATIONS

International Search Report and Written Opinion dated Nov. 26, 2008 for PCT Application No. PCT/US2008/064573, 19 pages.
International Preliminary Report on Patentability dated Aug. 7, 2009 for PCT Application No. PCT/US2008/064573, 8 pages.
Griss et al.: "Micromachined barbed spikes for mechanical chip attachment", Sensors and Actuators, Elsevier Sequoia S.A., Lausanne, CH, vol. 95, No. 2-3, Jan. 1, 2002, pp. 94-99.
Partial International Search Report dated Sep. 16, 2008 for PCT Application No. PCT/US2008/064573, 5 pages.

* cited by examiner

*Primary Examiner* — Linda Dvorak
*Assistant Examiner* — Brian M Antiskay
(74) *Attorney, Agent, or Firm* — Clause Eight IPS; Michael Catania

(57) ABSTRACT

Embodiments relate to methods and systems for monitoring bioelectric potentials. In some instances, an electrode is applied to a patient's skin. The electrode may be at least partly inserted into the patient's skin, such as by inserting at least part of one or more teeth underneath the skin.

34 Claims, 17 Drawing Sheets

METHOD AND DEVICE FOR QUICK PRESS ON EEG ELECTRODE

CROSS-REFERENCE TO RELATED APPLICATIONS

This application claims priority to U.S. Provisional Application No. 60/939,523, filed May 22, 2007, which is hereby incorporated by reference in its entirety.

BACKGROUND OF THE INVENTION

1. Field of the Invention

Embodiments relate to methods and systems for monitoring bioelectric potentials. In some instances, an electrode is applied to a patient's skin. The electrode may be at least partly inserted into the patient's skin, such as by inserting at least part of one or more teeth underneath the skin.

2. Description of the Related Technology

Electroencephalography (EEG) is a major clinical diagnostic tool used to evaluate cerebral function in humans. Briefly, one or more electrodes placed on the scalp detect electrical activity produced by the brain. This activity is transmitted to amplification and/or recording devices. The electrical activity is produced by the summation of neural activity across a plurality of neurons. Thus, monitoring of the amplitude and temporal dynamics of the electrical signals provides information about underlying neural activity and medical conditions associated with this activity.

For example, EEGs are commonly used to evaluate seizures, such as determining whether a seizure is an epileptic seizure or to localize the place of origin of the seizure within the brain. In another example, EEGs can be used to monitor sleep states or anesthesia depths. The neurobiological sciences are also using EEGs as a non-invasive research tool.

It may be necessary to keep the electrodes on for significant periods of time, such as during sleep monitoring. Additionally, because EEG monitoring usually comprises signals from multiple electrodes, each of a plurality of electrodes may need to be simultaneously secured to a patient's scalp. Furthermore, in some instances, the electrodes should maintain contact with the patient's scalp despite movement, such as that which may occur during a seizure. Therefore, there is a need to ensure that the EEG monitoring systems are stable and easy to use.

SUMMARY OF THE INVENTION

In some embodiments, an electrode is provided, the electrode comprising a main portion; a plurality of legs extending from said main portion; and a plurality of protrusions extending from each of said legs.

In some embodiments, an electrode system is provided, the system comprising: a plurality of electrodes, each of the electrodes comprising a main portion; a plurality of legs extending from said main portion; and a plurality of protrusions extending from each of said legs; and support structure to support the plurality of electrodes, wherein said system is configured to be worn on a patient's head.

In some embodiments, a kit is provided, the kit comprising a plurality of electrodes, each of the electrodes comprising a main portion; a plurality of legs extending from said main portion; and a plurality of protrusions extending from each of said legs; support structure to support the plurality of electrodes; a wireless transmitter; and a receiver configured to receive signals from the wireless transmitter, wherein said system is configured to be worn on a patient's head.

In some embodiments a method for recording biopotentials is provided, the method comprising: inserting part of an electrode into a patient's skin; and receiving a plurality of biopotentials by the electrode.

In some embodiments, an electrode is provided, the electrode comprising a plurality of protruding portions configured to stabilize the electrode upon attaching the electrode to a patient, wherein the electrode comprises a shape-memory material.

In some embodiments, an electrode system is provided, the system comprising: an applicator; and the electrode comprising a plurality of protruding portions configured to stabilize the electrode upon attaching the electrode to a patient, wherein the electrode comprises a shape-memory material.

DETAILED DESCRIPTION OF CERTAIN EMBODIMENTS

Figure 1:
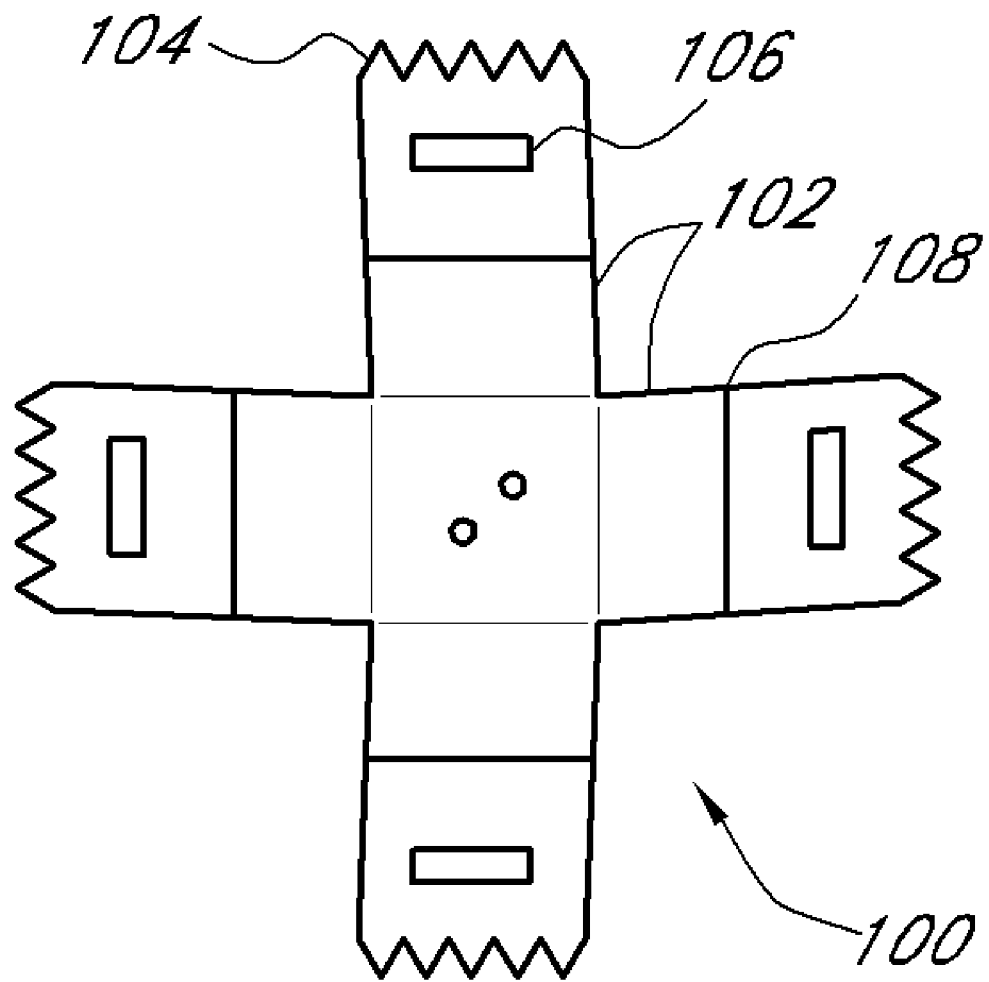
FIG. 1 is a top view of an example of an electrode according to one embodiment.

Typically, an EEG is made in contact with the scalp by first abrading the scalp with a gritty paste in order to lessen the skin's intrinsic electrical impedance, and then applying a conductive gel-containing or gel-filled electrode to the scalp. The electrode is then held in place by an adhesive. However, obtaining a stable electrode interface with good recording properties is a technically demanding process, a process that has required a trained EEG technologist in order to obtain recordings of satisfactory quality for clinical interpretation. Also, the successful application of EEG recoding electrodes is a time-consuming and thus expensive process, even for highly skilled EEG technologists. Small needles placed just under the skin (subdermal needles) have also been used for EEG recordings, but these too are time consuming to place, and their insertion induces a moderate amount of discomfort in patients who are not deeply obtunded or comatose. The difficulties involved in obtaining a satisfactory EEG electrode connection to the patient have limited the settings and scope of EEG recording, and in particular have limited the presence of EEG recording in intensive care units, emergency rooms, and emergent field settings, all locations in which evaluations of brain activity can provide diagnostically and therapeutically useful information.

Embodiments disclosed herein relate to electrodes that penetrate into the patient's skin in order to both provide attachment of the electrode to the patient and enhance transmission of biopotentials to external amplification and recording devices. Embodiments further provide a recording electrode which is durable and can be applied without skin preparation and without the use of conductive electrolyte gels.

The quality of EEG recordings (and biopotential recordings in general) can be degraded due to properties of the skin. The skin is composed of two primary layers, the dermis and epidermis; the hypodermis, a region of loose connective and adipose tissues connecting the epidermis and dermis to the underlying structures, is also sometimes considered as the third and deepest layer of the skin.

The epidermis, or outmost layer, is only, on average, about 50 microns thick on the scalp and consists of several stacked layers: deepest is the stratum basale, over which lies, in ascending order towards the surface, the stratum spinosum, stratum granulosum, stratum lucidum, and finally, abutting air, the stratum corneum.

The most superficial layer—the stratum corneum—has a high electrical impedance, which can act to reduce the amplitude of potentials recorded for an EEG. The stratum corneum (and the stratum lucidum) do not contain living cells and are largely responsible for the protection of the underlying skin layers from damage. Additionally, when a patient moves, the electrically charged nature of the skin can cause fluctuations in the skin's intrinsic electrical potential, thereby interfering with the signals of interest. The skin layer associated with movement-related alterations of the skin's electrical potential appears to be in the region of the thin stratum granulosum.

The dermis lies beneath the epidermis, and, at 1,000-2,000 microns thick, accounts for most of the mass of the skin. The dermis can be subdivided into two layers: the papillary layer and the reticular layer. The thin papillary layer sits just beneath the epidermis, and is composed of many connective tissue cells, blood-conveying microscopic capillaries, and collagen fibers. It is of note that the overlying epidermis does not contain blood-conveying vessels. Deep to the dermal papillary layer is the reticular layer of the dermis, a thicker and less cellular region that contains abundant collections of collagen fibers as well as the blood-conveying capillaries, arterioles, and venules. Nerve fiber endings mediating the sensations of touch, vibration, temperature sensation, and pain are present in both the dermis and in the epidermis. These nerve endings extend to about the boundary between the stratum granulosum and the stratum corneum (i.e., nerve endings are not evident in the most superficial layer of dead cells forming the skin's outermost surface).

Reduction in the skin's electrical impedance can be accomplished through abrasion of the skin with sandpaper, through puncturing the skin with a very short (500 micron) stylet, or thorough abrading of the skin with a gritty abrasive paste (the latter being the most commonly used clinical procedure). Common to these procedures is a relative breach of the superficial stratum corneum layer of the epidermis. All of these methods can cause skin irritation, and, if vigorous, a very small amount of localized transient bleeding. However, virtually all clinical EEG recording utilizes one of these methods to reduce the skin's impedance.

FIG. 1 shows a top view of an embodiment of an electrode 100. The electrode 100 comprises four legs 102 extending from a main portion of the electrode 100. The main portion may comprise a central portion of the electrode 100 and/or a portion from which all legs 102 extend. Each leg comprises one or more teeth 104 or protrusions that are configured to penetrate a patient's skin as described herein. The illustrated embodiment of the electrode 100 includes five teeth 104. Other embodiments may include any other suitable number of teeth. The teeth may have sharp points as illustrated in FIG. 1 or the teeth may have other shapes or wider or shallower points. The electrode may include one or more slots 106 for use in conjunction with an applicator, as shown, for example, in FIG. 4. Each leg 102 may also have one or more score lines 108 to facilitate even bending of the legs 102. In some embodiments, a diameter or length of the main body of the electrode 100 is at least about 0.1, 0.2, 0.3, 0.4 or 0.5 cm and may be less than or equal to about 3, 2.5, 2, 1.5 or 1 cm. Smaller size electrodes may be suitable for, for example, very young children. The length of the teeth 104 may be at least 50, 100, 200, 300 400 or 500 microns and may be less than or equal to about 1000, 900, 800, 700, 600 or 500 microns. The teeth may be long enough to extend through the epidermis and anchor the electrode when it is flattened. The length and width of the legs 102 relative to the diameter of the electrode 100 may vary, for example, so that the legs 102 be bent to an angle of at least about 20, 25, 30 or 35 degrees and/or less than or equal to about 60, 55, 50, 45 or 40 degrees. The angle may be an angle relative to the surface of the main body and/or to the position of the unbent legs. The angle may also be an insertion or an attack angle, describing the angle at which the legs are relative to a patient's skin upon insertion of the electrode 100. The electrode 100 may be substantially flat in shape when ultimately residing on the skin. The electrode 100 may be manufactured using, for example, electroetching and/or microlaser manufacturing procedures.

The electrode 100 may comprise a thin metal, such as a moderately electrically conductive alloy. In one embodiment, the electrode 100 comprises a nitinol or other suitable shape memory material, metal or alloy. An electrode comprising one or more of these materials, metals or alloys may be bendable or deformable but may subsequently move towards its initial shape. For example, legs of an electrode comprising a shape memory metal may be configured to bend upon application of a force (e.g., a force applied by a human or machine prior to insertion of the electrode into a patient's skin) and to return towards an initial configuration upon release of said force (e.g., after the electrode has been inserted into the patient's skin). The legs may be bent away from the plane of an electrode body prior to insertion into a patient and may return towards this plane, such that the legs lie substantially parallely under a patient's skin after insertion, securing the position and insertion of the electrode.

In some instances (e.g., when the electrode comprises a shape memory alloy), the electrode may be compatible with computerized tomographic (CT) and magnetic resonance (MR) imaging studies; such that a patient wearing the electrode (e.g. a critically ill or unstable patient) does not need to remove the electrode before undergoing such studies. In one embodiment, the metal is at least about 0.0005, 0.001, 0.002 or 0.003 inches in thickness and/or less than or equal to about 0.020, 0.015, 0.010, 0.008, 0.007, 0.006, 0.005 or 0.004 inches in thickness. The natural or "remembered" shape of the electrode 100 in such an embodiment is a flat, substantially planar geometry. To apply the electrodes, the legs 102 may be each bent at an angle (e.g., about 25, 30, 40, 45 or 50 degrees) and pressed into the skin of the patient so that the teeth 104 enter the skin at a shallow angle (e.g. about 0 to about 45°). Once inserted, the memory properties of the electrode 100 tend to force the legs 102 back into their planar position, thus causing the surface of the teeth 104 to push out against the skin. This force helps to hold the electrode 102 in place.

In another embodiment, the electrode 100 comprises stainless steel. The legs 102 of the steel electrode 100 are bent at an angle (e.g., about 25, 30, 40, 45 or 50 degrees) and pushed into the skin with enough force to at least partly flatten the legs 100 and affix the electrode 100. In other embodiments, the electrode may be formed of any suitable conductive material, or combination of materials, with at least a portion of the electrode being formed of a conductive material. For example, other embodiments may comprise a nonconductive material with a conductive outer material.

The electrode 100 may be used to record EEG data from a human or an animal patient. The electrode 100 may be used to record other bioelectric potentials accessible at the skin, including the electrocardiogram. In some embodiments, the electrode 100 can be successfully and painlessly placed on hair-containing or hairless skin within seconds, establishes a long-lasting and stable electrical connection, does not require conductive gel for stable recording, and/or is self-anchoring.

Figure 2:
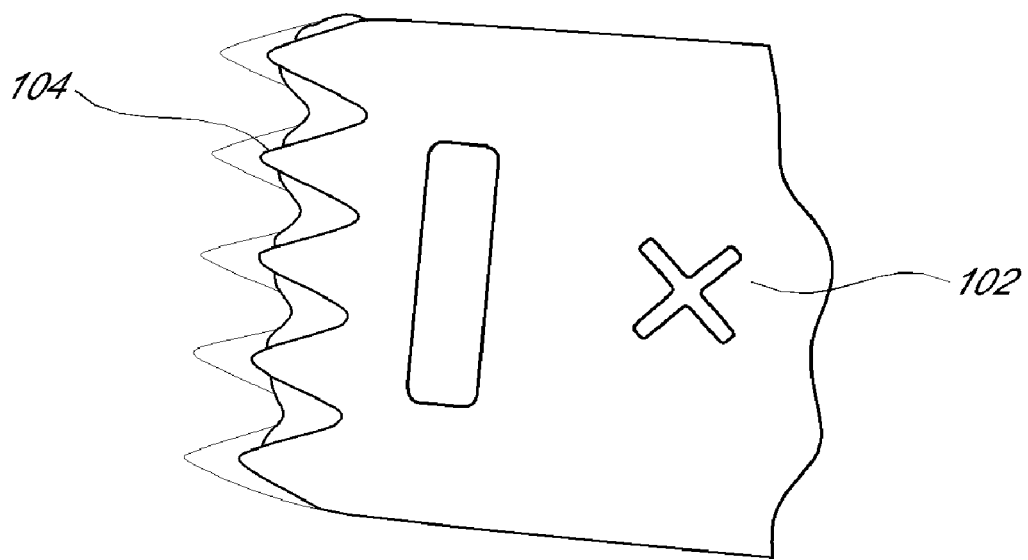
FIG. 2 is a top view of the electrode of FIG. 1 inserted in skin of a human.

FIG. 2 is a top view of the electrode 100 inserted in skin of a human. The teeth 104 are partly under the skin thereby affixing the electrode 100.

Figure 3:
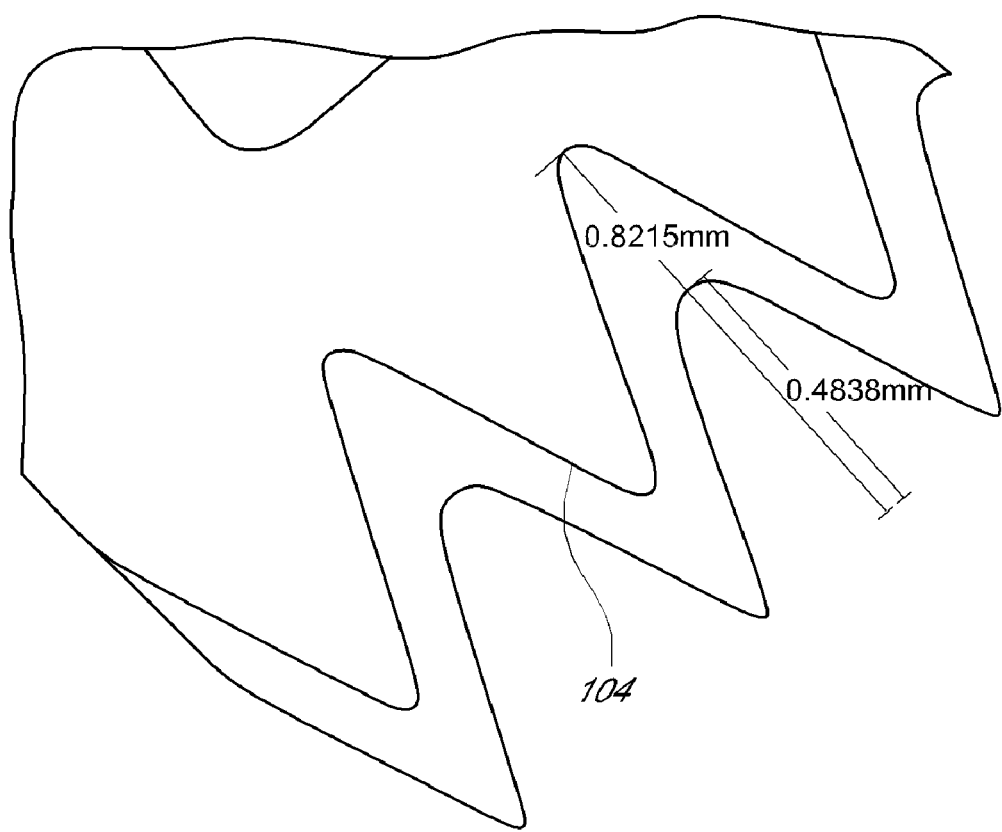
FIG. 3 is a top view further illustrating the teeth of an electrode such as illustrated in FIG. 1.

FIG. 3 is a top view illustrating the teeth 104 of the electrode 100. In the illustrated embodiment, a portion 302 of the teeth 104 has been etched to form thin, sharp edges and points along the edge of the etched portion 302 to easier insertion of the electrode 100 into the skin.

Figure 4:
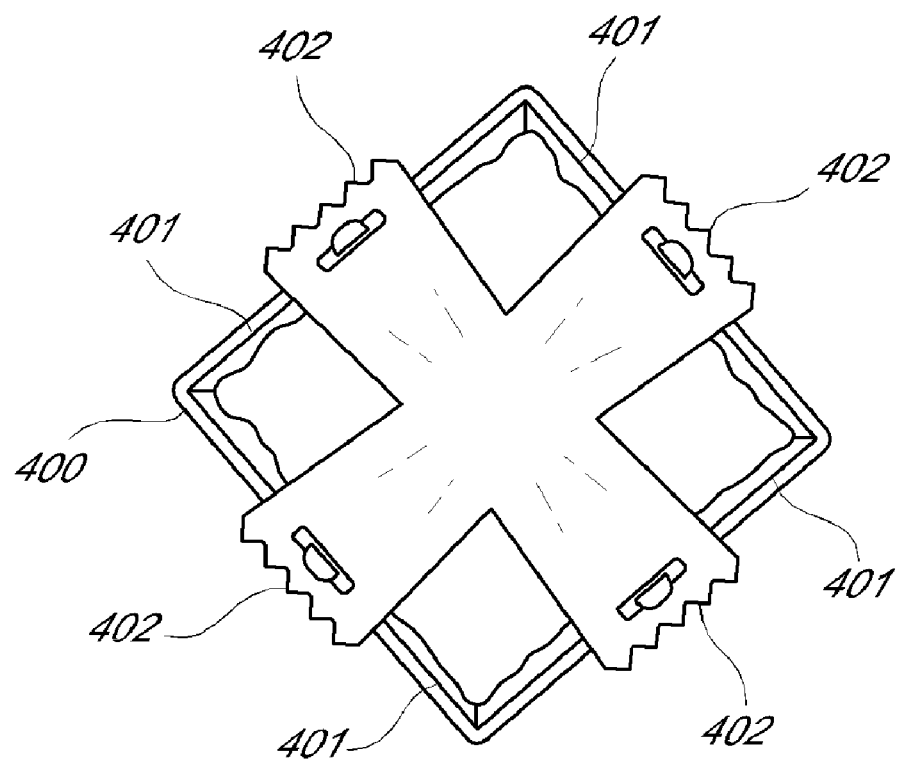
FIG. 4 is a bottom view further illustrating one embodiment of an electrode such as illustrated in FIG. 1 in a device for applying the electrode.

FIG. 4 is a bottom view the electrode 100 positioned in a device or applicator 400 configured to apply or affix the electrode 100 to a medium (e.g., a patient's skin). The illustrated applicator 400 comprises one or more sides 401 that each have a radially extending flange or tab 402 configured to fit into the slots 108 of the legs 102 of the electrode 100 when the legs 102 are bent for insertion. The applicator 400 may include an insertion triggering component, such as a button or actuator, (not shown) on the opposite side of the applicator 400 that is configured to eject an electrode 100 (e.g., upon depression of a button) from the applicator 400, for example into a patient's skin. In the illustrated applicator 400, the applicator 400 includes a recess 406 into which the electrode 100 is forced, bending the legs 102, until the tabs 402 engage the slots 108. This action helps to bend the legs 102 to a selected angle for insertion. The electrode 100 and/or applicator 400 are configured such that when the electrode 100 is applied to the patient's skin, the electrode 100 depresses (e.g., via the button or actuator) so that the teeth 104 are forced into the patient's skin and so that the legs 102 bend sufficiently for the legs 102 to be released from the tabs 402. The applicator 400 can thus allow easier and/or more consistent bending of the legs 102 for insertion and application of pressure to insert the electrode 100.

Figure 5:
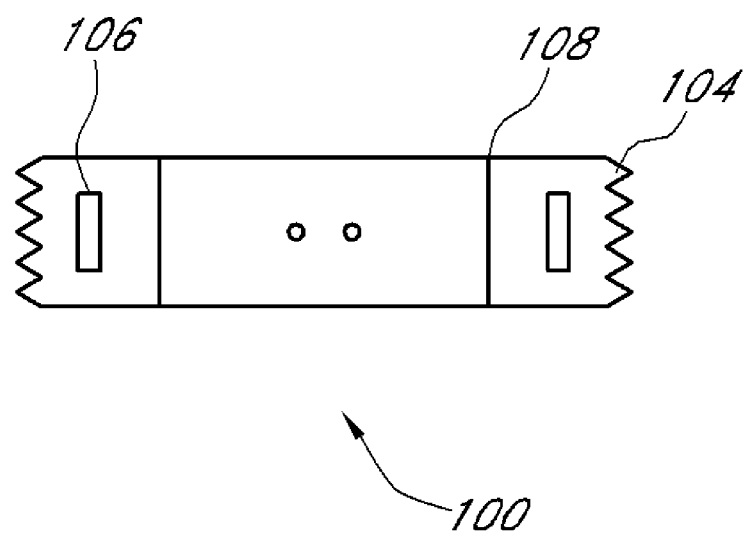
FIG. 5 is a top view of another example of an electrode according to one embodiment.

FIG. 5 is a top view of another example of the electrode 100. In the embodiment illustrated in FIG. 5, the electrode has two legs 102 (instead of 4 legs of the example of the electrode 100 illustrated in FIGS. 1-4. It is to be recognized that other embodiments may have different numbers of legs 102 and/or teeth 104.

As illustrated in FIG. 1, the electrode 100 comprises a small central planar metallic portion from which several in-plane extensions (legs) 102 protrude outward. These legs 102 are tipped by a row of several small sharp beveled teeth 104 oriented outwards from the electrode's center. Initially, the peripheral portion of the electrode's legs 102 are bent symmetrically out of plane with the electrode's center, either with a physical bend or utilizing the flexible properties of shape memory alloys. This allows the leg's terminal teeth 104 to approach the skin at an angle of attack of, for example, 30-45 degrees relative to the skin's surface. When the electrode 100 is pressed downward with an application device or by hand, its teeth penetrate the skin in an orientation roughly parallel to the skin's surface to a depth of, for example, approximately 100-330 µm, and the overall electrode configuration flattens onto the skin's surface. The embedded teeth can form the point of electrical contact between the patient and an amplification and recording system. Because of the radial orientation of the legs 102 and teeth 104, this insertion process deforms the skin very slightly in a radial direction compared to the electrode's center and so anchors the electrode due to both the elasticity of the skin pressing back against the electrode's teeth 104 and rigid body, as well as by the resistance of the very thin superficial layer of skin lying directly over the electrode's multiple teeth. The electrode's electrical impedance may be, for example, at least about 1, 2, 3, 4, 5, 7 or 10 kΩ and/or may be less than or equal to about 50, 40, 30, 25, 20, 19, 18, 17, 16, 15, 12 or 10 kΩ. The electrode may also have substantially stable electrical interface resistance. EEG recordings attained through using an electrode 100 described herein may comprise fewer skin movement-related electrical artifacts. Though not wishing to be bound to any particular theory, this may be because it barely penetrates the barrier layer of epidermis to a sufficient depth. The electrode 100 may be relatively inexpensive and/or disposable (e.g., in embodiments in which the electrode comprises stainless steel). The electrode 100 may be durable and/or reusable (e.g., in embodiments in which the electrode 100 comprises nitinol and/or stainless steel). Reusable electrodes 100 may be configured to be disinfected across uses. The electrode 100 may be used, for example, in computed tomography and magnetic resonance imaging devices. Metals of the electrode 100 may be electroplated with silver or gold to increase conductivity. Further, in one embodiment in which the electrode 100 is electroplated with silver, the electrode 100 may be coated with silver-chloride (AgCl), which may optimize the transduction of Cl ions from the scalp to the electrons in the metal. Electrodes may be mass produced using, for example, photo chemical etching.

Figure 6:
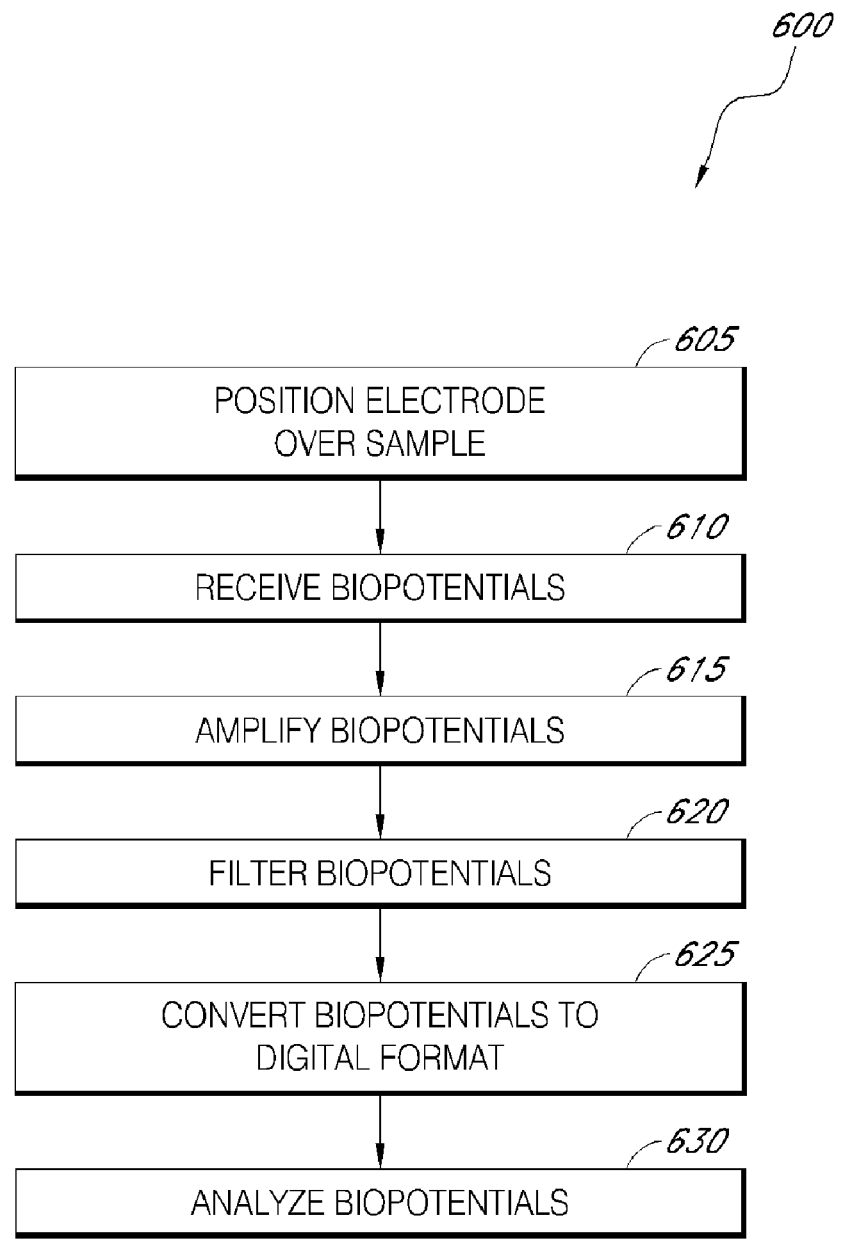
FIG. 6 illustrates a process for recording biopotentials.
Figure 7:
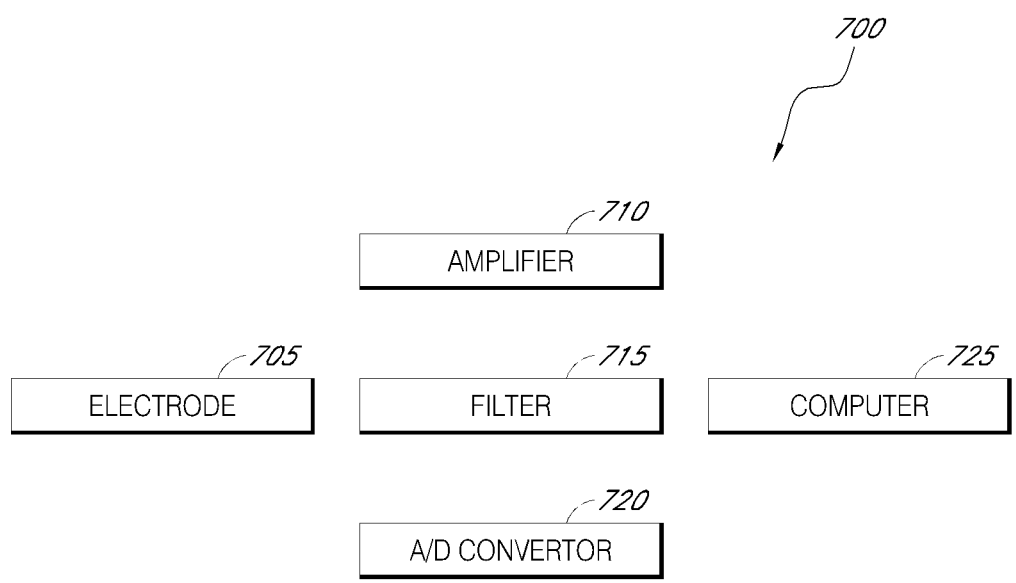
FIG. 7 shows a system for recording biopotentials.

FIG. 6 shows a process 600 for recording biopotentials, and FIG. 7 shows a system 700 for recording biopotentials. Process 600 begins at step 605 with the positioning of an electrode 705 over a sample. The electrode 705 may comprise any electrode 100 as described herein. The positioning of the electrode 705 may comprise inserting at least part of the electrode 705 into the sample. For example, at least part of one or more teeth of the electrode 705 may be inserted to be underneath a surface of the sample. At least part of the electrode 705 (e.g., a sharp end of one or more teeth) may puncture a surface of the sample. Teeth of the electrode 705 may be inserted into the sample such that the positions of the teeth once the electrode is positioned are approximately parallel and/or close to the surface of the sample. This may be possible due to a radial orientation of the teeth. In embodiments in which at least part of the electrode 705 punctures a sample surface, the puncturing (and the positioning of the electrode 705) may be associated with an acceptable amount, a negligible amount or no pain.

The positioning of the electrode 705 may comprise physically attaching the electrode 705 to the sample, such as by anchoring the electrode 705 to the sample using part of the electrode 705. The positioning of the electrode 705 may be such that the electrode 705 is then configured to remain substantially stationary relative to the sample, for example, throughout a sustained duration (e.g., about 15 minutes, 30 minutes, 45 minutes, 1 hour, 2 hours, 4 hours, 6 hours or 8 hours) or during movement of the sample or part of the sample (e.g., the patient's skin). In one instance, penetrations of electrode teeth into the epidermal layer reduce skin movement artifacts. The electrode 700 may remain more stationary as compared to other electrodes that are not at least partly inserted into the sample. In some embodiments, only a single electrode 700 is positioned, while in other embodiments a plurality of electrodes 700 are positioned. At least one of the plurality of electrodes may serve as a reference electrode, such that signals of other (signal) electrodes may be compared to signals of the reference electrode. The electrode 705 may be configured to be stably positioned to be substantially stationary relative to the sample within less than about 30, 20, 10, 5, 3, 2 or 1 second.

The electrode 705 may be positioned such that it lies substantially flat again a surface of the sample. In one instance, teeth of the electrode may be inserted through the sample's surface and the portion of the electrode 705 not inserted into the sample lies flat against the surface. This may reduce or eliminate cutaneous pressure points related to electrode 705 protrusions when head weight is applied to the flat electrode surface.

In some embodiments, the electrode 705 is positioned over the sample without the use of or with reduced use of a conductive gel or paste. For example, in one embodiment, the surface of the sample is not coated with a conductive gel or paste before the electrode 705 is positioned. In another embodiment, the surface of the sample is coated with less conductive gel or paste than would otherwise be used with a standard disc electrode. In some embodiments, no secondary adhesive is used to further stabilize the electrode 705 over the sample.

The sample may comprise a patient or a patient's skin. In some embodiments, the sample comprises a region of the patient of a patient's skin, such as the head or the scalp. For example, teeth of an electrode may be partly inserted into the scalp's skin of a patient, thereby puncturing a top layer or a surface of the skin and anchoring the electrode 705 to the patient. The sample may comprise hair. For example, the electrode 705 may be positioned over a region of a patient's scalp, that region containing hair. The small size and shape of the electrode 705 may enable hair to pass around the edges of the device. A large intra-cutaneous electrode recording surface may, in some embodiments, be provided by superficial skin penetration of multiple teeth of the electrode.

In some embodiments, the sample is not abraded. For example, in some embodiments, no skin abrasive has been used to prepare a surface of the sample for the positioning of the electrode 705.

The patient may comprise a mammal, such as a human. The patient may be suffering from a disease or medical condition or may be substantially healthy. The disease or medical condition may comprise an insomnia, sleep disorder, migraines, epilepsy, multiple sclerosis, schizophrenia, auditory neuropathy, a heart disease, muscular dystrophy, or a psychiatric condition.

Process 600 continues with step 610 with the receiving of a plurality of biopotentials by the positioned electrode 705. The electrodes 705 may be used in connection with, for example, ECG, EEG or EMG recordings to receive biopotentials of the heart, the brain or the muscle, respectively. Biopotentials may be received during a predefined time interval or during one or more tasks. For example, biopotentials may be received while a patient reads an eye chart, sleeps or exercises.

Next, at step 615 of process 600, the received biopotentials are amplified. The biopotentials may be amplified by an amplifier 710. The amount of amplification may depend on, for example, the signal being measured and/or noise.

Continuing to step 620 of process 600, the amplified biopotentials are filtered by one or more filters 715. The filters used in the filtering may depend on signal and/or noise properties. The amplifier 710 may comprise a filtering component to filter the biopotentials.

Moving to step 625 of process 600, the filtered biopotentials are converted to a digital format. Any appropriate A/D convertor 720 may be used to perform this conversion. The amplifier 710 may comprise a conversion component to convert the biopotentials to a digital format.

Proceeding to step 630 of process 600, the converted biopotentials are analyzed. In one embodiment, the converted biopotentials are input to a computer 725. The computer 725 may then analyze the converted biopotentials and/or may store or output biopotential data (e.g., on a screen or a printer) to allow a user to analyze the data. The biopotential data may comprise one or more time-varying voltage traces or frequency spectra obtained from the converted biopotentials. The analysis may comprise a diagnosis or evaluation of a disease or medical condition. The analysis may comprise a state determination (e.g., a sleep state or an anesthesia state) of a patient. The analysis may comprise an evaluation of an organ or a patient, such as the health of a heart or of a human. In some embodiments, the converted biopotentials are used to produce electroencephalograph, electrocardiograph, or electromyograph data.

Steps of the process 600 may be added, deleted, combined, or rearranged. For example, in some embodiments, the filtering step 620 is deleted. In some embodiments, the amplifying and filtering steps are combined or reversed with respect to each other. Similarly, system 700 may have fewer or more components than as presented here, and separate components may be combined.

Figure 8A:
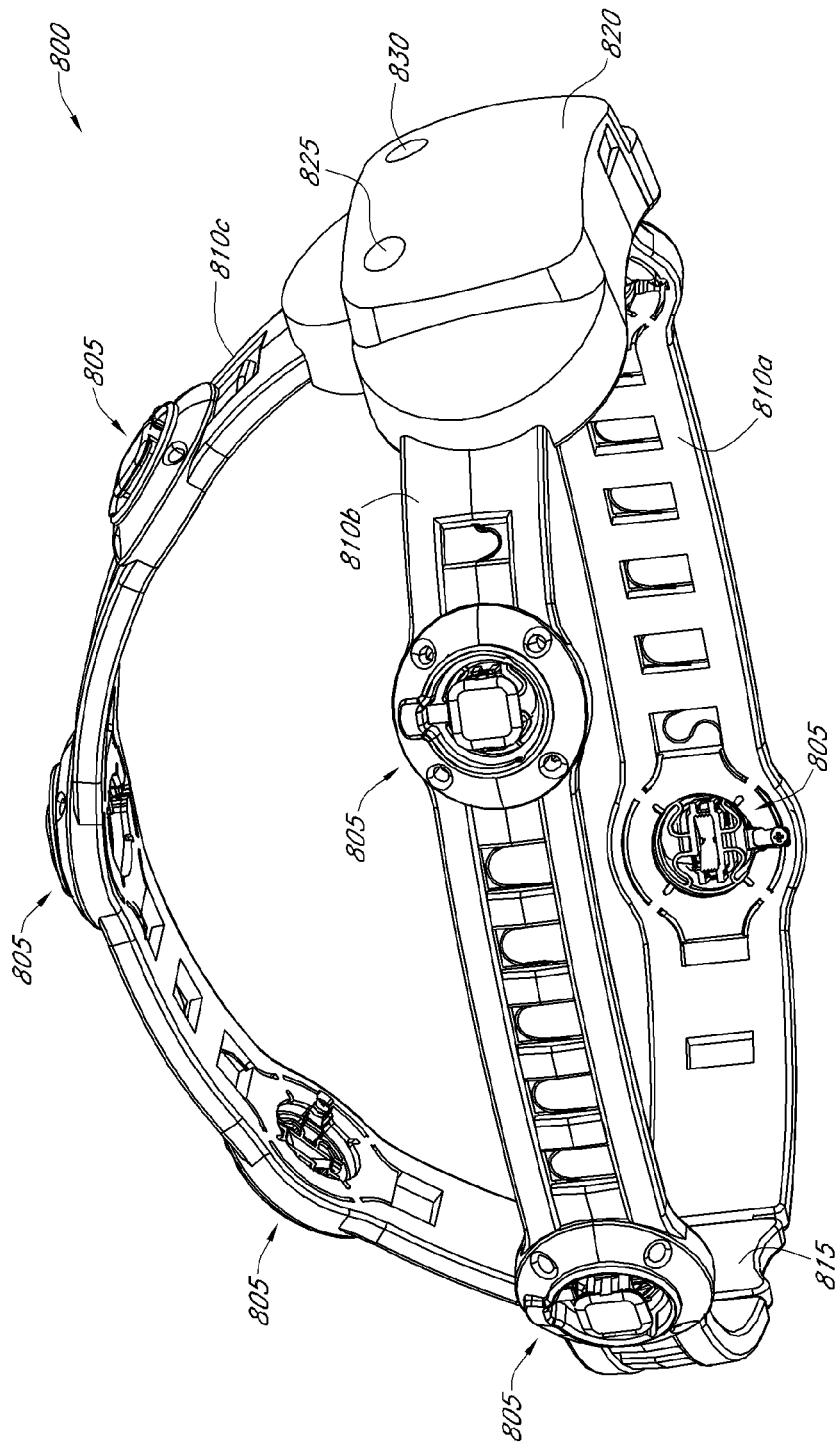
FIGS. 8A-H show a biopotential recording system and electrode components in the system.
Figure 8B:
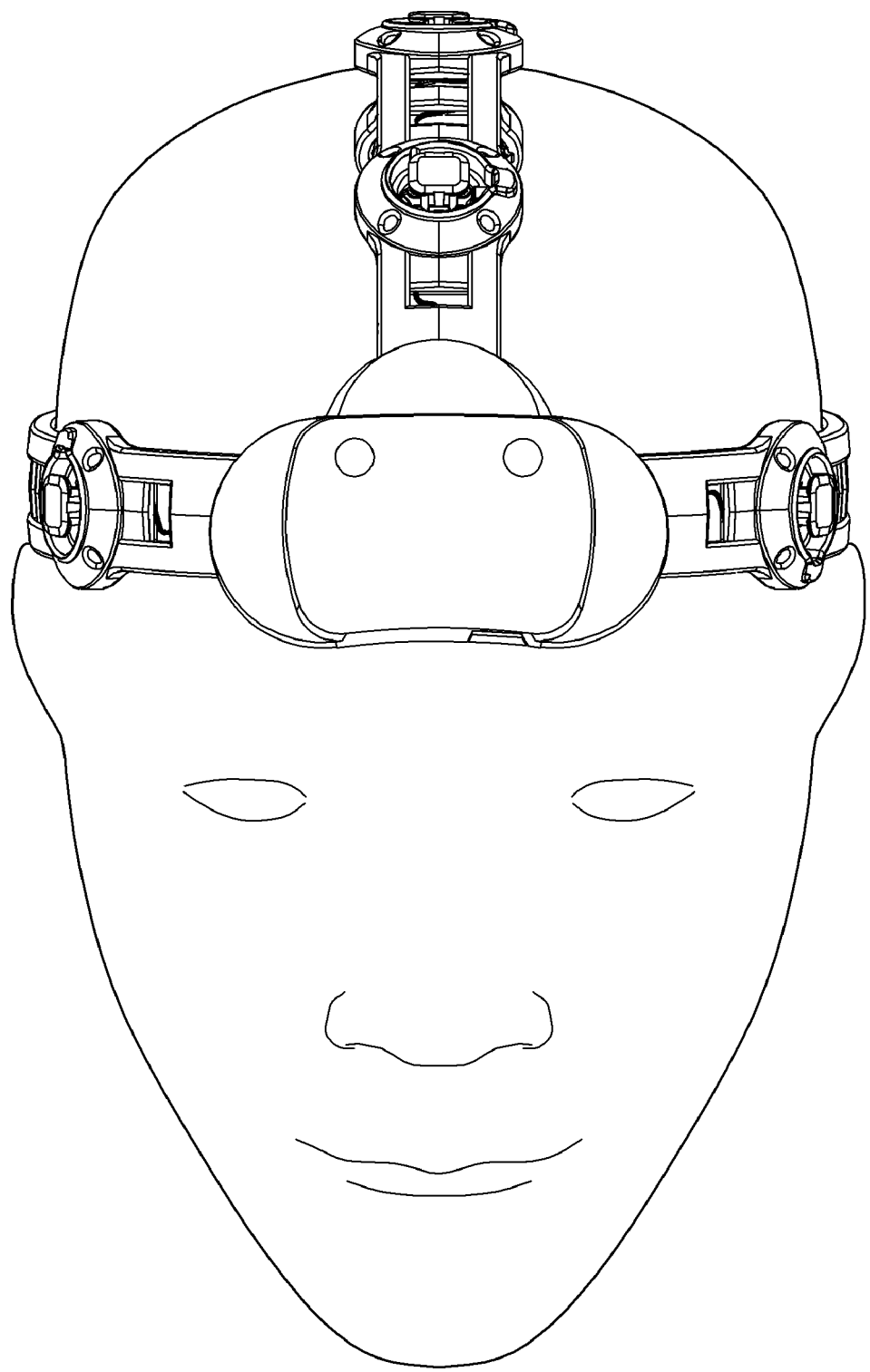
Figure 8C:
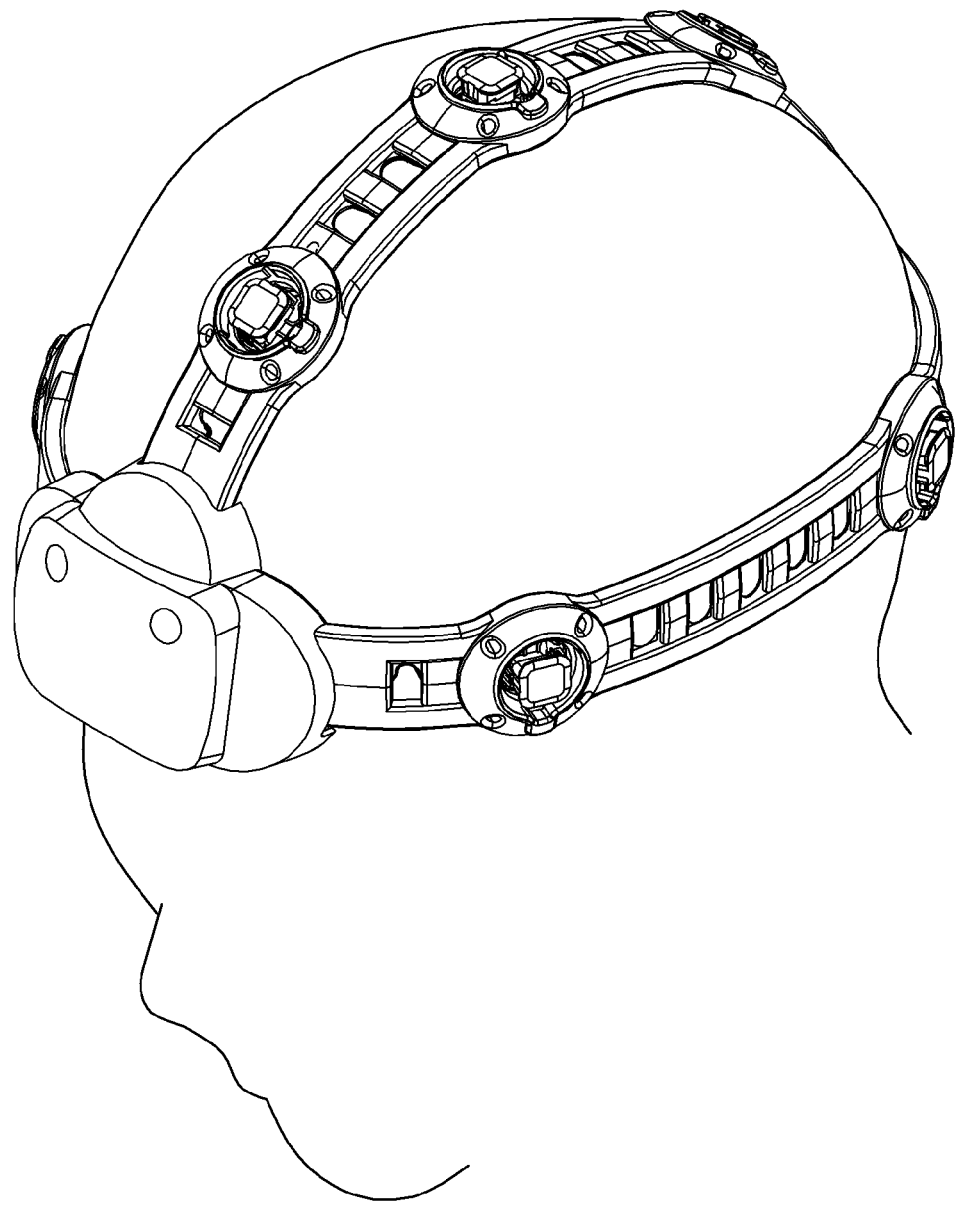
Figure 8D:
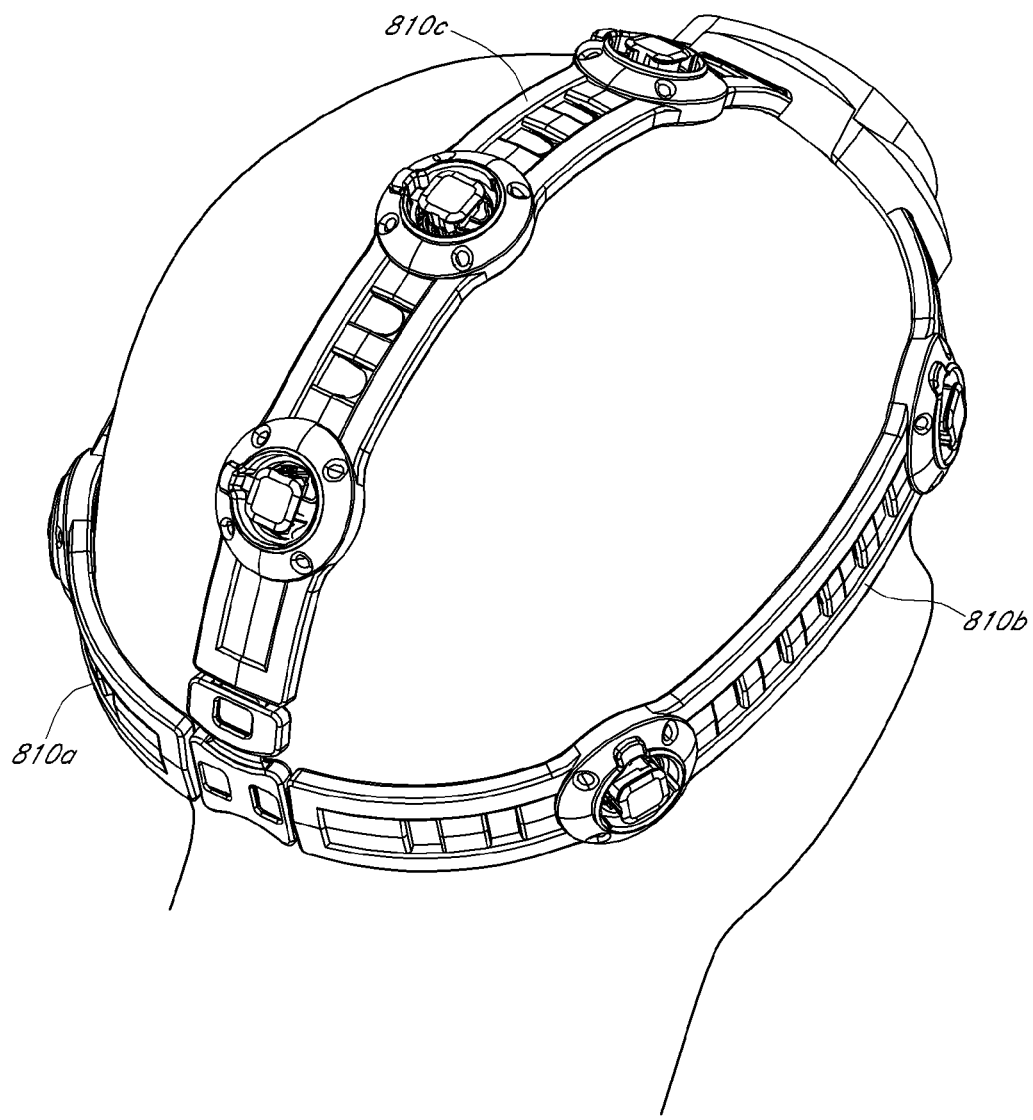
Figure 8E:
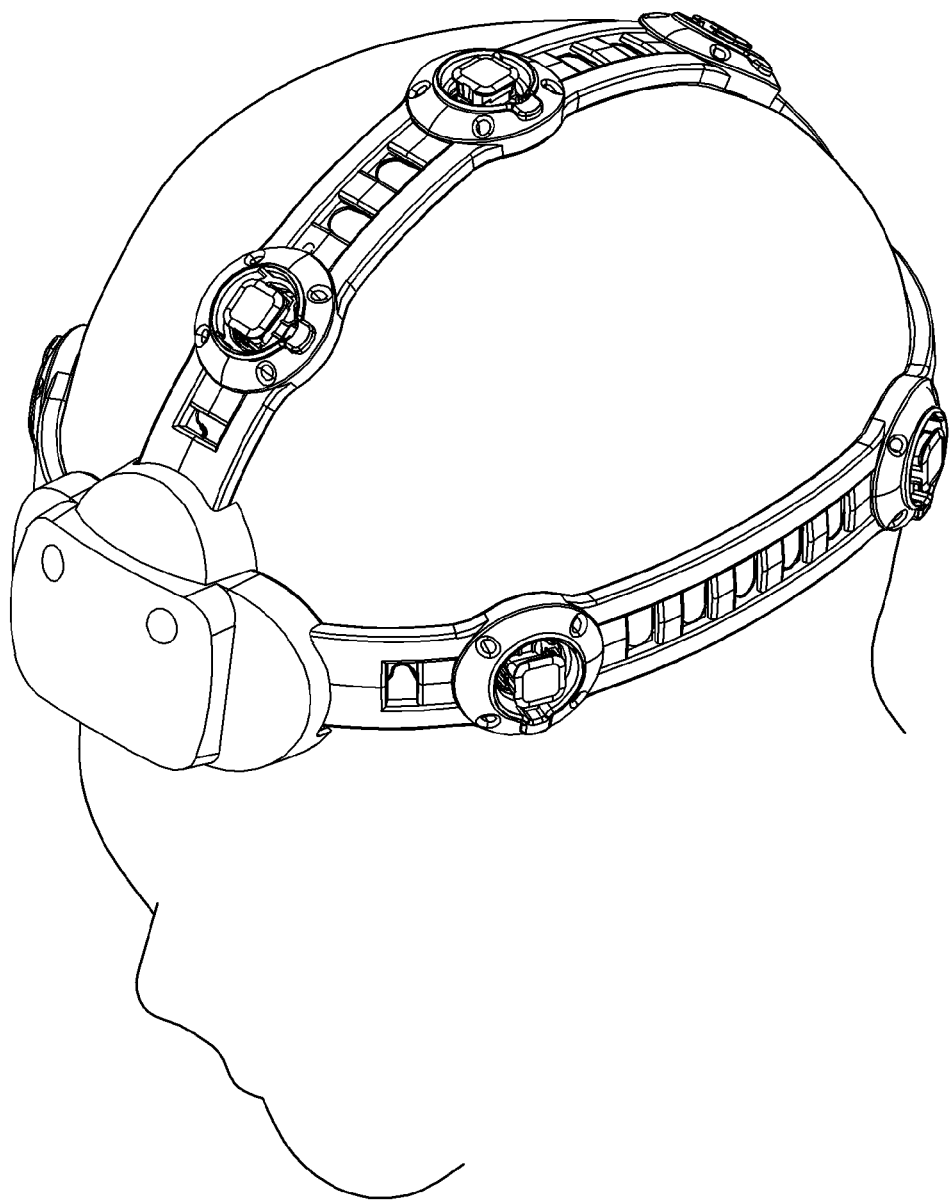

FIG. 8A shows a biopotential recording system 800 comprising a plurality of electrode components 805. The system shown in FIG. 8 may be configured to be worn by a patient, as shown in FIG. 8B-E. The system may be configured such that parts of the electrode components of the system can be inserted into the skin of a patient's head. The system may comprise a headpiece, at least one head bands and/or at least one strap. FIGS. 8A-E show an embodiment where the system comprises a headpiece comprising three straps 810a-c. Two straps 810a-b are configured to wrap around a patient's head, while a third strap 810c is configured to be positioned on top of a patient's head. The straps may be connected by a strap securing component 815. In some embodiments, each strap 810 snaps into the strap securing component 815. The system 800 may comprise a size-adjusting mechanism. The size-adjusting mechanism may be configured to change the length of a band, a circumference of a headpiece of another dimension of the system. The size-adjusting mechanism may include, for example, a belt with a number of holes, such that a lock could be secured through one of the holes to adjust a size of the system 800.

The system 800 may comprise flexible material and/or rigid material. For example, straps 810a-c may be flexible in order to bend around a patient's head. The system may comprise support structure (e.g., straps 810a-c) to support electrode components to maintain specific spacing between electrode components or positions of the electrode components. The support structure may also house wiring or connections, such as that between electrode components and/or between electrode components and another device.

The system 800 may comprise a power supply 820. The power supply 820 may include, for example, one or more batteries or a connection to an external power source. In some embodiments (e.g., ones which utilize battery power) the system 800 is portable. The system 800 may include one or more controls, such as a power control 825. The power control 825 or other controls may, in some embodiments, also be used to perform other functions, such as specifying active electrodes or a recording type. The system may include one or more indicators 830. The indicator may indicate, for example, that the system is powered and/or that electrodes are properly positioned and/or inserted. The indicator may be a visual indicator and may, for example, a light source.

Figure 8F:
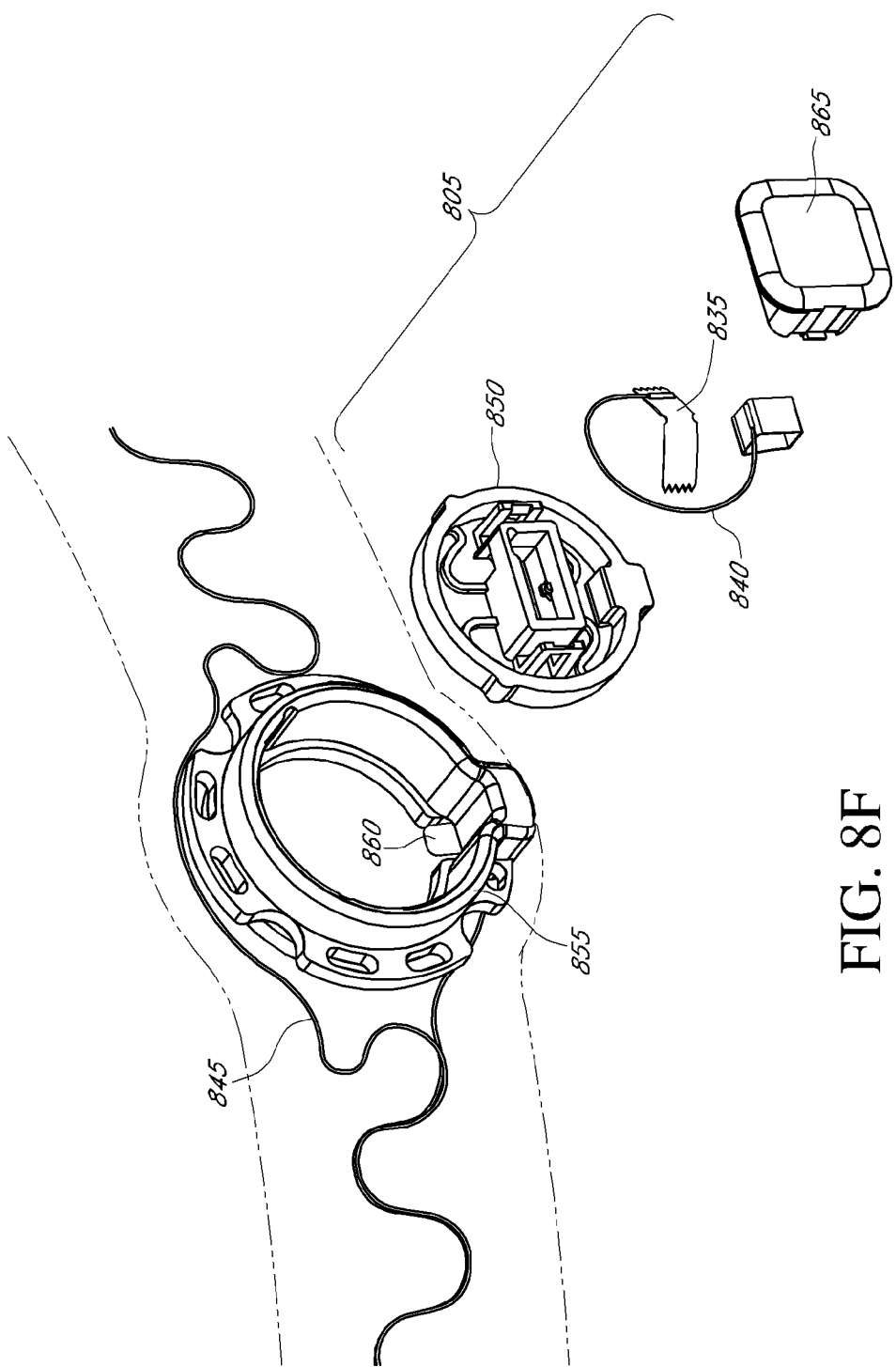
Figure 8G:
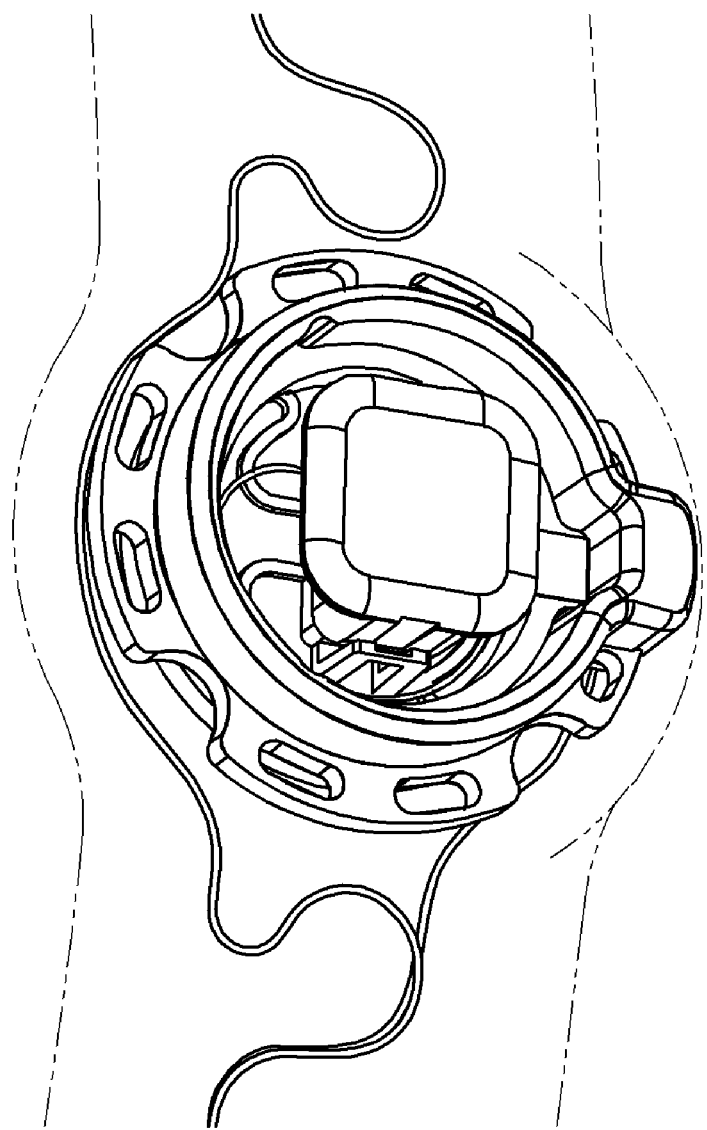
Figure 8H:
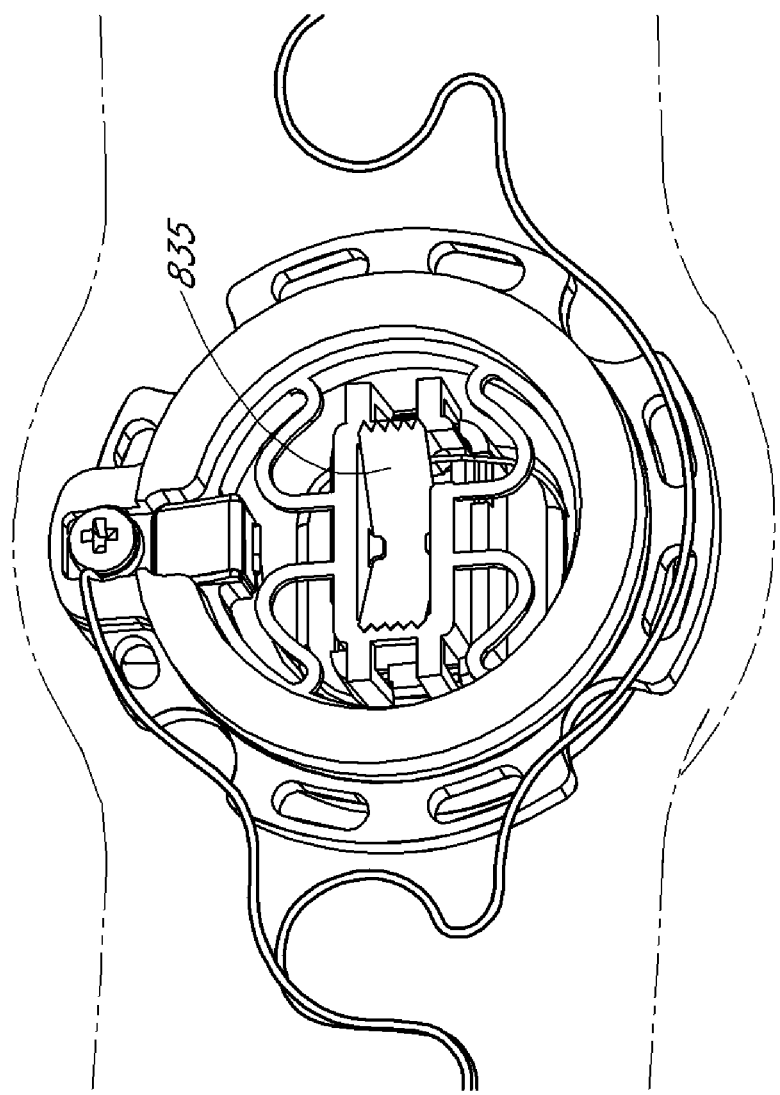

FIGS. 8F-H show exploded expanded views of an electrode component 805. The electrode component comprises an electrode 835, such as an electrode described herein. The electrode 835 shown in FIG. 8F comprises two legs and five protrusions extending from each leg. An electrode connector 840 is connected to the electrode 835. The electrode connector 840 may comprise a conductive material, such as copper foil The electrode connector 840 may connect the electrode to wiring 845. The wiring 845 may serve to transmit signals between electrodes and/or from the system 800. The electrode 835 may be positioned within a suspension structure 850 or another support. The suspension structure 850 or support may support the electrode 835 within the system 800. For example, the suspension support 850 is configured to fit within a ring 855 in order to securely support the electrode 835 within the system 800. The suspension structure may be configured to support the electrode 835 when the electrode 835 is bent or in an unrelaxed state. However, in some instances, the suspension structure 850 is configured such that movement of the electrode 835 from an unrelaxed state towards a relaxed state causes the electrode 835 to be ejected from the suspension structure 850.

A flexible conductive piece 860 may be positioned within the ring. The piece 860 may comprise, for example, a metal or alloy, such as nitinol. The piece 860 may provide electrical contact from the electrode 835 with the wiring 845. A material that doesn't fatigue after repeated bending may be used in the piece 860 to ensure that strong contact will be maintained after repeated electrode replacements.

The electrode component may also include an applicator 865. The applicator may comprise, for example, a button or a switch. Triggering of the applicator 865 (e.g., by pushing a button) may cause at least part of the electrode 835 to be inserted in a patient (e.g., a patient's scalp).

In some embodiments parts or all of the electrode component 805 are removable from the system 800. Thus, between patients or recording periods, new electrodes may be inserted into the electrode component or the electrodes may be positioned into a compressed, unrelaxed state, such that the electrodes 835 are again ready to be attached to the patient.

FIG. 8H shows a compressed, unrelaxed electrode. Upon pressure on the button, the electrode may be forced at least partly out of the suspension support 850, the protrusions of the electrode 835 piercing a patient's skin. The electrode 835 may then return towards a relaxed state, in which both legs are substantially in the same plane.

The system 800 may be lightweight, weighing less than about 10, 5, 4, 3, 2, 1, ½ or ¼ pounds. The system 800 may include a transmitter. The transmitter may be a physical connection or a wireless transmitter. The transmitter may transmit data to a receiver (e.g., a digital, USB-powered receiver), which may be connected to, for example, to a computer. The receiver may be small, such as less than about 5, 4, 3, 2, 1, ½ or a ¼ inch in its largest dimension. The receiver and/or transmitter may be configured such that the wireless operating range is at least about 0, ¼, ½, 1, 2, 3, 4, 5, 8, 10 or 20 meters and/or no greater than about 100, 50, 30, 20, 15 or 10 meters.

The system 800 may comprise a storage component or a memory in order to store biopotential recording data. The system 800 may comprise an amplifier, a filter and/or an A/D converter.

In some embodiments, a kit may comprise an electrode or system 800 described herein. The kit may further comprise leads and/or connectors. The leads and/or connectors may be configured to connect the electrode to an electronic device, such as an amplifier. The kit may comprise an amplifier, filter and/or A/D converter. The kit may comprise a computer (e.g., a portable computer). The computer may comprise software for analyzing biopotential recordings.

Figure 9A:
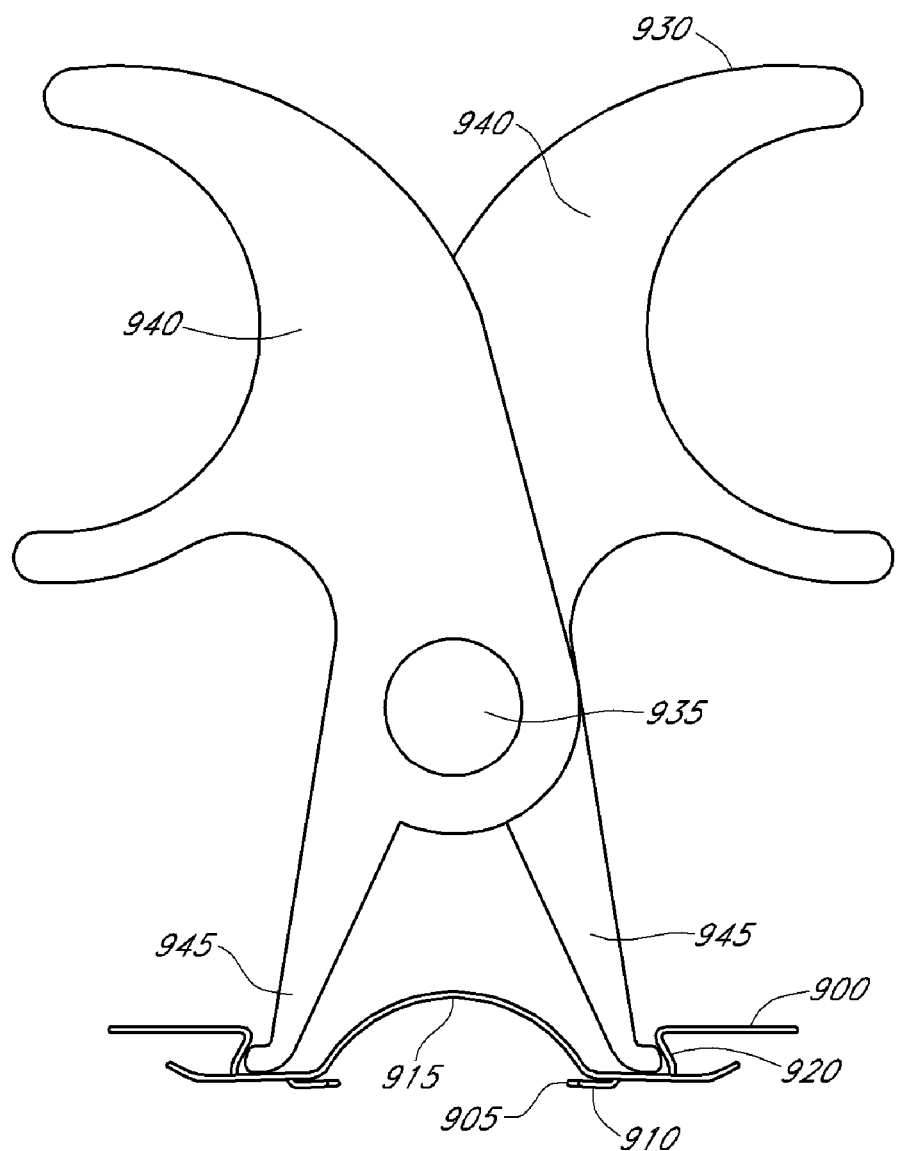
FIGS. 9A-B show an example of an electrode and an applicator according to one embodiment.
Figure 9B:
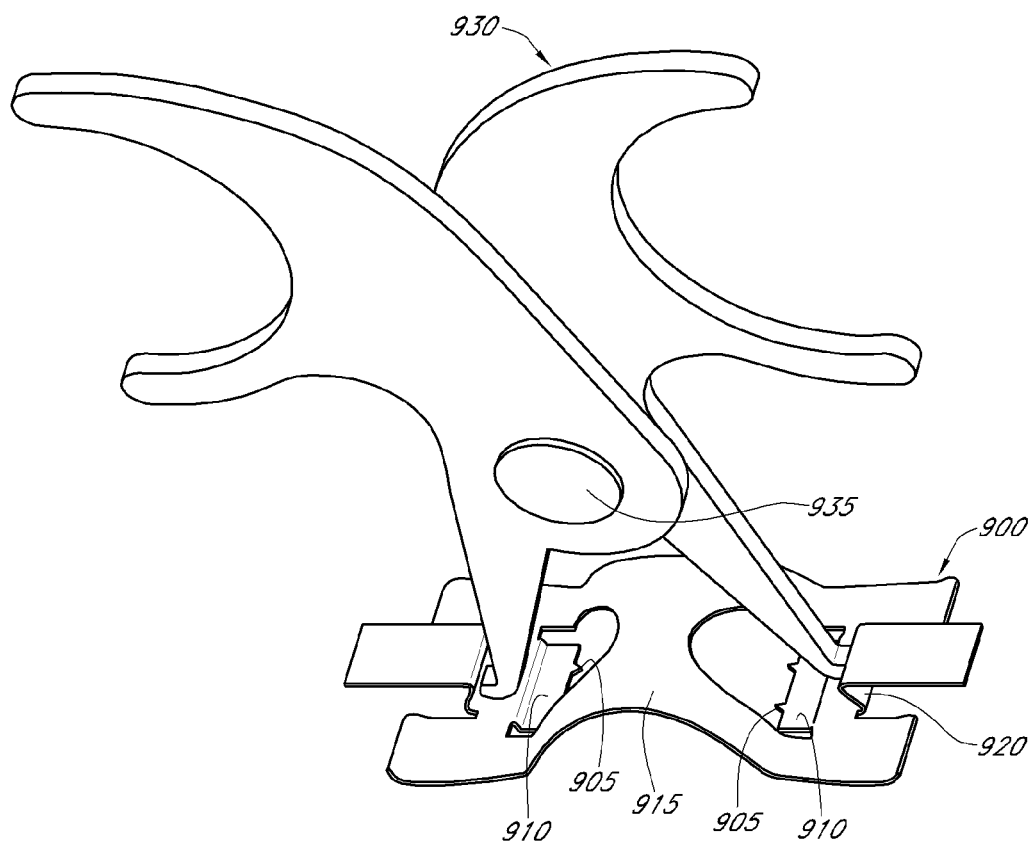

As described above, an electrode may be configured such that the electrode expands following the initial insertion of the electrode (upon a release of an applied force). Alternatively, the electrode may be configured to contract following the initial insertion of the electrode. For example, as shown in FIGS. 9A-B, an electrode 900 may be configured such that the electrode 900 is expanded upon application of a force (e.g., prior to inserting the electrode in a patient) and is compressed upon removal of the force (e.g., after the insertion). The electrode 900 comprises a plurality of protruding portions 905 or teeth. The protruding portions 905 may have characteristics of protrusions or teeth as described herein. For example, the length of the protruding portions 905 may be at least 50, 100, 200, 300 400 or 500 microns and may be less than or equal to about 1000, 900, 800, 700, 600 or 500 microns. The protruding portions 905 may be configured to stabilize, position and/or anchor the electrode 900 after at least part of the electrode has been inserted into a sample or patient or after the electrode has been attached to a sample or patient. In some embodiments, two or more segments 910 comprise the protruding portions 905. The segments 910 may be positioned substantially symmetrically around a central portion of the electrode 900. For example, in FIG. 9B, two segments 910 are shown to be positioned on opposite sides of a central curved portion 915. The protruding portions 905 may be positioned on the inner surface of the segments 910, as shown in FIG. 9B, such that the protruding portions 905 of multiple segments 910 are facing each other and pointing towards a central portion of the electrode 900.

The electrode 900 may comprise a deformable, flexible and/or shape memory material. As used herein, a shape memory material refers to a material that can be deformed from an initial state to a deformed state upon application of a force between but returns towards the initial state upon release of the force. In FIG. 9A-B, the electrode 900 comprises a central curved portion 915 which is deformable. Application of force may cause the radius of the curved portion 915 to expand. For example, a downward force may be applied to the central curved portion 915 while an upward force is applied to the sides of the electrode 900. In some embodiments, at least one force is applied to the electrode 900 prior to the application, attachment and/or insertion of the electrode 900 in a patient. When the electrode contacts a patient, the at least one force may be released, which may reduce the radius of curvature of the central curved portion 915, thereby reducing the separation between the segments 910, and puncturing the patient's skin with the protruding portions 905. Thus, the protruding portions 905 may then anchor or stabilize the electrode 900 in the patient. Notably, the electrode 900 may be configured such that following application of the electrode, portions of the electrode 900 (e.g., the protruding portions 905) are inserted into a patient, while other portions (e.g., the curved circular portion 915) are not.

In some embodiments, the electrode is made of only a single material, whereas in other embodiments, the electrode comprises a plurality of materials. The electrode may comprise, for example, stainless steel or an alloy. The electrode 900 may be manufactured by an assembly line. For example, a stainless steel electrode may be cut, stamped and sharpened on an assembly line. The electrode 900 may comprise one or more removal tool contact portions 920. The removal tool contact 920 may comprise, for example, a groove, to maintain stable contact between a removal tool 930 and the electrode 900.

The removal tool 930 may be configured to apply force to the electrode 900 and/or to change the distance between at least two of the protruding portions 905 and/or at least two of the segments 910. In one instance, when force is applied to the removal tool 930, force is also applied to at least two applicator contact removal tool contact portions 920, which then increases the separation between at least two segments 910 and increases a radius of curvature of the central curved portion 915. This may cause protruding portions 905 or portions of the protruding portions 905 that are in a patient (e.g., punctured through a patient's scalp) to be removed from the patient, thereby unattaching the electrode 900 and the patient.

In one embodiment, the removal tool 930 comprises at least one pivot point 935. The removal tool 930 may comprise at least one force application component 940 and at least one or at least two electrode contact components 945. The force application components 940 may be configured such that force may be applied to one or all of the components by an operator (e.g., a human) or a machine. In some embodiments, such as the embodiment shown in FIGS. 9A-B, the force application components 940 comprise a curved surface. The force application components 940 may be configured such that the distance between at least two force application components 940 decreases upon application of a force. The electrode contact components 945 may be configured such that a distance between the electrode positioning components is at least partly dependent on force applied to the at least one force application component. For example, application of a force on the force application components 940 may increase the separation distance between the electrode contact components. In some embodiments, the applicator 930 is separable from the electrode 900.

Embodiments of the electrode include an easily applied self-anchoring electrode for recording bioelectric potentials present at the skin's surface. In some embodiments, an electrode as described herein may serve as a replacement for a standard EEG disc recording electrode, a subdermal needle EEG electrode, and/or a subdermal wire EEG electrode. Moreover, the infection risk associated with such electrodes that penetrate the epidermis or superficially into the dermis would not be expected to be greater than with standard disc EEG electrodes (a risk which is very low, and which is minor in severity when a rare case of superficial skin infection does occur).

Embodiments of an electrode as described herein may be used for applications that include: any suitable applications and settings in which EEG might be performed (EEG laboratory, epilepsy monitoring unit, intensive care unit, operating room, emergency room, emergency field settings, and ambulatory EEG monitoring); any suitable applications and settings in which cerebral evoked potentials or event-related potentials might be performed, including for psychiatric and psychological studies; use as the point of person-machine contact in a device acting as a brain-machine interface; and settings in which EEG or evoked potentials might be performed on animals.

While the above detailed description has shown, described, and pointed out novel features of the invention as applied to various embodiments, it will be understood that various omissions, substitutions, and changes in the form and details of the device or process illustrated may be made by those skilled in the art without departing from the spirit of the invention. As will be recognized, the present invention may be embodied within a form that does not provide all of the features and benefits set forth herein, as some features may be used or practiced separately from others.

What is claimed is:

1. An electrode comprising: a main portion defining a plane; a plurality of legs extending from said main portion and away from the plane; and a plurality of protrusions extending from each of said legs wherein said legs are configured to bend, upon application of a force, towards the plane so as to define a substantially flat shape in an attack configuration and to return towards an initial configuration upon release of said force, wherein said electrode comprises a shape memory material.

2. The electrode of claim 1, wherein said legs are bendable such that the distal end of each leg moves away from the main portion upon application of the force.

3. The electrode of claim 1, wherein the length of said protrusions is between about 300 to about 600 microns.

4. The electrode of claim 1, wherein said protrusions comprise sharp points configured to penetrate skin of the patient.

5. The electrode of claim 1, wherein said electrode comprises stainless steel.

6. The electrode of claim 1, wherein said electrode comprises an alloy.

7. The electrode of claim 1, wherein said electrode comprises a nitinol.

8. The electrode of claim 1, wherein said electrode is between about 0.002 and about 0.010 inches thick.

9. An electrode system, the system comprising:
a plurality of electrodes according to claim 1; and
support structure to support the plurality of electrodes,
wherein said system is configured to be worn on a patient's head.

10. The electrode system of claim 9, further comprising a power supply.

11. The electrode system of claim 9, further comprising at least one of an amplifier, a filter and an A/D converter.

12. The electrode system of claim 9, further comprising a wireless transmitter.

13. The electrode system of claim 9, wherein said support structure comprises a plurality of straps configured to be wrapped around the patient's head.

14. A kit comprising:
a plurality of electrodes according to claim 1;
support structure to support the plurality of electrodes;
a wireless transmitter; and
a receiver configured to receive signals from the wireless transmitter,
wherein said system is configured to be worn on a patient's head.

15. An electrode comprising: a main portion defining a plane; a plurality of legs extending from said main portion and away from the plane; and a plurality of protruding portions extending from each of said legs and configured to stabilize the electrode upon attaching the electrode to a patient, wherein said legs are configured to bend, upon application of a force, towards the plane so as to define a substantially flat shape in an attack configuration and to return towards an initial configuration upon release of said force, wherein the electrode comprises a shape-memory material.

16. The electrode of claim 15, wherein at least two of said protruding portions are configured to be separated by a first distance upon application of a force and to be separated by a second distance upon release of said force, said first distance being greater than said second distance.

17. The electrode of claim 15, wherein the length of said protruding portions is between about 300 to about 600 microns.

18. The electrode of claim 15, wherein said protruding portions comprise sharp points.

19. The electrode of claim 15, wherein said electrode comprises stainless steel.

20. The electrode of claim 15, at least two of said protruding portions are connected by a flexible curved electrode component.

21. The electrode of claim 20, wherein the electrode is configured such that a radius of said flexible curved electrode component is larger during application of a force than during release of said force.

22. An electrode system, the system comprising: a removal tool; and an electrode comprising a main portion defining a plane; a plurality of legs extending from said main portion and away from the plane; and a plurality of protruding portions extending from each of said legs and configured to stabilize the electrode upon attaching the electrode to a patient, wherein said legs are configured to bend, upon application of a force, towards the plane so as to define a substantially flat shape in an attack configuration and to return towards an initial configuration upon release of said force, wherein the electrode comprises a shape-memory material.

23. The electrode system of claim 22, wherein said removal tool comprises a pivot point.

24. The electrode system of claim 22, wherein said removal tool comprises at least one force application component and at least two electrode contact components,
wherein a distance between the at least two electrode contact components is at least partly dependent on force applied to the at least one force application component.

25. The electrode system of claim 24, wherein said at least one force application component comprises two force application components, and wherein said applicator is configured such that a distance separating the at least two electrode contact components increases as the distance between the two force application components decrease.

26. An electrode comprising: a main portion defining a plane; a plurality of legs extending radially from said main portion; and a plurality of protrusions extending radially from each of said legs, said main portion, said legs and said protrusions lying in said plane when in an initial configuration, wherein said legs are configured to bend away from said plane upon application of a force to said electrode from said initial configuration to an attack configuration wherein said legs do not lie in said plane, and to return towards said initial configuration upon release of said force, whereby, when said electrode is placed against skin of a patient, said protrusions insert into said skin of said patient upon said electrode returning from its attack configuration to its initial configuration and secure said electrode to said skin of said patient; wherein said electrode comprises a shape memory material.

27. The electrode of claim 26, wherein said legs contain score lines to facilitate even bending of said legs.

28. The electrode of claim 26, wherein the lengths of said protrusions are between 300 to 600 microns.

29. The electrode of claim 26, wherein said protrusions are sharp points.

30. The electrode of claim 26, wherein said electrode is between 0.002 and 0.010 inch thick.

31. The electrode of claim 26, wherein said protrusions are beveled.

32. The electrode of claim 26, wherein said plurality of legs extends symmetrically from said main portion.

33. The electrode of claim 32, wherein said plurality of legs is three legs.

34. The electrode of claim 31, wherein said attack angle is at least 32 degrees relative to said initial configuration.

* * * * *